United States Patent [19]
Hermentin et al.

[11] Patent Number: 4,948,880
[45] Date of Patent: Aug. 14, 1990

[54] ANTHRACYCLINE DERIVATIVES HAVING CYTOSTATIC ACTIVITY

[75] Inventors: Peter Hermentin, Marburg; Michael Paal, Hamburg; Hans P. Kraemer; Cenek Kolar, both of Marburg; Dieter Hoffmann, Lahntal; Manfred Gerken, Marburg; Hans G. Berscheid, Schwalbach am Taunus; Dirk Böttger, Liederbach, all of Fed. Rep. of Germany

[73] Assignee: Behringwerke Aktiengesellschaft, Marburg, Fed. Rep. of Germany

[21] Appl. No.: 129,006

[22] Filed: Dec. 4, 1987

[30] Foreign Application Priority Data
Dec. 8, 1986 [DE] Fed. Rep. of Germany ....... 3641833

[51] Int. Cl.$^5$ .......................................... C07H 15/252
[52] U.S. Cl. .................................................... 536/6.4
[58] Field of Search ........................................ 536/6.4

[56] References Cited
U.S. PATENT DOCUMENTS
| | | | |
|---|---|---|---|
| 4,245,045 | 1/1981 | Umezawa et al. | 435/886 |
| 4,591,637 | 5/1986 | Acton et al. | 536/6.4 |
| 4,737,583 | 4/1988 | Huber et al. | 536/6.4 |

OTHER PUBLICATIONS
Tanaka et al., *Journal of Antibiotics*, vol. 35, No. 3, 1982, pp. 312–321.
Tong et al., *J. of Medicinal Chemistry*, vol. 22, No. 8, 1979, pp. 912–918.
Essery et al., *Can. J. Chem.*, vol. 58, 1980, pp. 1869–1874.
Tavoloni et al., *J. Pharm. Pharmacol.*, vol. 32, 1980, pp. 860–862.
Williams et al., *Photochemistry and Photobiology*, vol. 34, 1981, pp. 131–134.
Oki et al., *J. of Antibiotics*, vol. 32, No. 8, 1979, pp. 801–819.
Yoshimoto et al., *J. of Antibiotics*, vol. 37, No. 8, 1984, pp. 920–922.
T. Oki, Microbial Transformation of Anthracycline Antibiotics and Development of New Anthracyclines, Anthracycline Antibiotics, 1982, pp. 75–96.
Essery et al., Can. J. Chem., vol. 58, 1980, pp. 1869–1874.

*Primary Examiner*—Ronald W. Griffin
*Assistant Examiner*—Pamela S. Webber
*Attorney, Agent, or Firm*—Finnegan, Henderson, Farabow, Garrett, and Dunner

[57] ABSTRACT

The invention relates to new anthracycline derivatives having cytostatic activity and the general formula I, which are optionally in the form of a salt of an inorganic or organic acid,

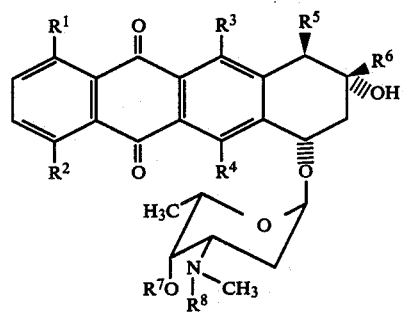

in which the substituents have the following meaning:
$R^1$ is hydrogen or a hydroxyl group,
$R^2$ is hydrogen or a hydroxyl or a methoxy group,
$R^3$ is hydrogen or a hydroxyl group,
$R^4$ is hydrogen or a hydroxyl group,
$R^5$ is hydrogen, a hydroxyl or a methoxycarbonyl group, or a substituent of the general formula II,

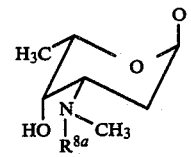

in which $R^{8a}$ has the meaning indicated for $R^8$, or a substituent of the formula III,

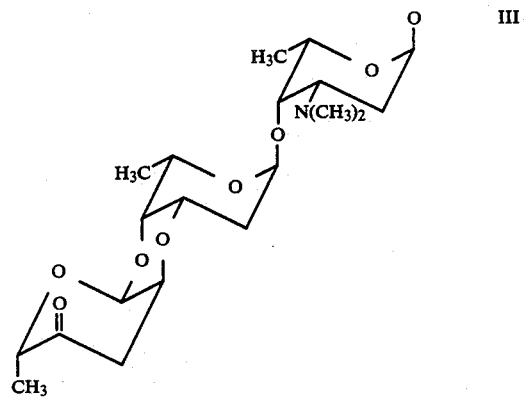

$R^6$ is ethyl, methylcarbonyl, hydroxymethylcarbonyl, hydroxyalkyl or a dihydroxyalkyl,
$R^7$ is hydrogen or a substituent of the general formula IV, (Abstract continued on next page.)

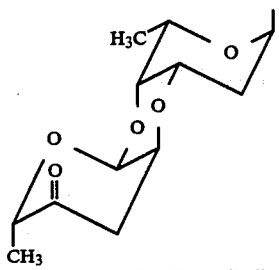
IV and $R^8$ is hydrogen or a cyanomethyl group or a substituent of the general formula $COR^9$ or $CH_2R^{10}$, $R^9$ being hydrogen, $CH_3$, $CF_3$ or $CCl_3$, and $R^{10}$ being $C_1$- to $C_8$-alkyl, substituted alkyl, phenyl or substituted phenyl, to a process for their preparation and to their use in pharmaceuticals.
16 Claims, No Drawings

ANTHRACYCLINE DERIVATIVES HAVING CYTOSTATIC ACTIVITY

The invention relates to new anthracycline derivatives having cytostatic activity, to a process for their preparation, and to their use in pharmaceuticals.

The anthracycline class of substances has been known for a long time now. Since the establishment of the structure of the rhodomycins, of adriamycin and of daunomycin, and the recognition of the cytostatic activity of certain representatives of the latter anthracycline class, a large number of anthracyclines has been obtained by biological means from representatives of the Actinomycetes genus streptomyces, and their action has been investigated.

It is known that some anthracyclines such as, for example, adriamycin, daunomycin, aclacinomycin, 4'-epi-adriamycin, 4'-methoxyadriamycin or 4'-deoxyadriamycin, have already been used for the therapy of tumors. It is common to these compounds that they carry in position 7 of the relevant aglycone either the sugar α-L-daunosamine (for example in the anthracyclines adriamycin, daunomycin and 4-demethoxyadriamycin) or the sugar α-L-rhodosamine (for example in the anthracyclines N,N-dimethyldaunomycin, aclavin or β-rhodomycin I). Also known are anthracyclines which carry in position 7 of the relevant aglycone an α-L-daunosamine unit which is substituted on the 3'-amino group (for example in the anthracyclines N-trifluoroacetyladriamycin, N-benzyladriamycin, N,N-dibenzyladriamycin, morpholinodaunomycin, cyanomorpholinodaunomycin or cyanomorpholinoadriamycin).

Known in addition are anthracyclines which have in position 7 of the aglycone a trisaccharide unit, such as, for example, aclacinomycin A, as well as anthracyclines which, besides a trisaccharide unit in position 7 of the aglycone, also have a monosaccharide or trisaccharide unit in position 10 of the aglycone, such as, for example, cytorhodin S or cytorhodin P.

It is common to these compounds that the sugar unit which is bonded at position 7 or position 10 of the aglycone is always α-L-rhodosamine.

Finally, U.S. Pat. No. 4,591,637 additionally discloses compounds of the following formula I in which $R^1$=H, $R^2$=H, OH or —OCH$_3$, $R^3$=$R^4$=OH, $R^5$=H, $R^6$=ethyl, methylcarbonyl, hydroxymethylcarbonyl, hydroxyalkyl or dihydroxyalkyl, $R^7$=H, and $R^8$ is a cyanomethyl group.

A considerable problem in the use of these known anthracyclines for tumor therapy is that, besides the desired cytostatic activity, they have undesired side effects such as, for example, hematological or cardiac toxicity.

Based on this state of the art, the object of the present invention is to provide new anthracycline derivatives which, where possible, are not cross-resistant with respect to adriamycin and which are distinguished by a new spectrum of action and a lower toxicity than adriamycin, and thus can be used advantageously in tumor therapy.

This object according to the invention has been achieved with new anthracycline derivatives having cytostatic activity and corresponding to the following general formula (I)

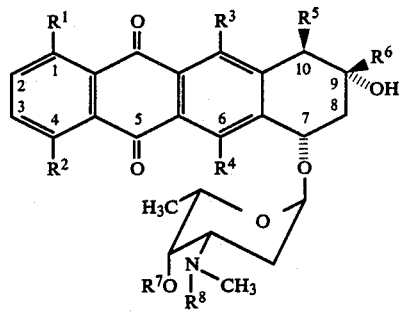

and which are optionally in the form of a salt of an inorganic or organic acid, and in which the substituents have the following meanings:

$R^1$ is hydrogen or a hydroxyl group,
$R^2$ is hydrogen or a hydroxyl or a methoxy group,
$R^3$ is hydrogen or a hydroxyl group,
$R^4$ is hydrogen or a hydroxyl group,
$R^5$ is hydrogen, a hydroxyl or a methoxycarbonyl group, or a radical of the general formula II,

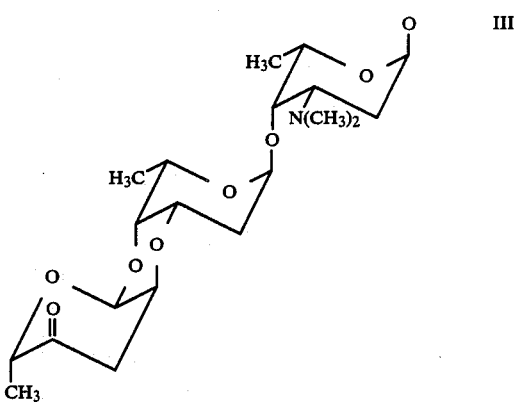

in which $R^{8a}$ has the meaning indicated for $R^8$, or a substituent of the formula III, $R^6$ is ethyl, methylcarbonyl, hydroxymethylcarbonyl, hydroxyalkyl or dihydroxyalkyl,
$R^7$ is hydrogen or a substituent of the general formula IV,

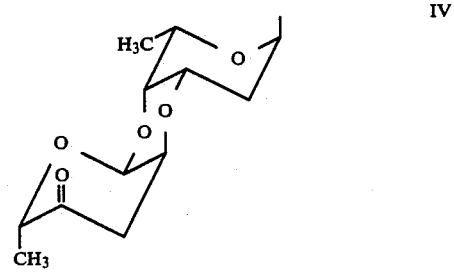

$R^8$ is hydrogen or a cyanomethyl group or a substituent of the general formula $COR^9$ or $CH_2R^{10}$, $R^9$ being hydrogen, $CH_3$, $CF_3$ or $CCl_3$, and $R^{10}$ being $C_1$-to $C_8$-alkyl, substituted alkyl, phenyl or substituted phenyl, excepting the compound of the formula I in which $R^1=H$, $R^2=OH$, $R^3=H$, $R^4=OH$, $R^5=COOCH_3$, $R^6=CH_2CH_3$ and $R^7=R^8=H$, and, for the additional case where $R^8$ is a cyanomethyl group, those compounds in which $R^1$ is H, $R^2$ has the said meaning, $R^3$ is OH, $R^4$ is OH, $R^5$ is H, $R^6$ has the said meaning, and $R^7$ is H.

In this connection, the substituents can be present on the phenyl radical in the ortho, meta or para position, and examples which may be mentioned are: methyl, ethyl, hydroxyl, methoxy, ethoxy, nitro, cyano, fluoro, chloro or bromo.

In particularly preferred aglycone derivatives of the present invention, the substituents in the abovementioned formula have the following meanings:

$R^1$ to $R^4$ and $R^6$ as indicated above, $R^5$ hydrogen, a hydroxyl or a methoxycarbonyl group, $R^7$ hydrogen, and $R^8$ hydrogen, cyanomethyl or a substituent of the general formula $COR^9$, with $R^9$ equal to H, $CH_3$, $CF_3$ or $CCl_3$, or a substituent of the general formula $CH_2R^{10}$, $R^{10}$ being $C_1$-to $C_8$-alkyl, substituted alkyl, phenyl, or substituted phenyl which is substituted in the ortho, meta or para position by methyl, ethyl, hydroxyl, methoxy, ethoxy, nitro, cyano, fluorine, chlorine or bromine.

Further particularly preferred anthracycline derivatives are evident from subclaims 3 to 20, which optionally may be in the form of adducts with physiologically acceptable inorganic or organic acids.

The process according to the invention for the preparation of the new anthracycline derivatives having cytostatic activity starts from anthracycline compounds which can be obtained by biological means (T. Oki in Anthracycline Antibiotics, H. S. El Khadem, ed., Academic Press 1982, page 75) and which either are directly available in the form of the rhodosamine derivative or are obtained in a straightforward manner by N,N-dimethylation of the corresponding daunosaminyl-anthracyclinone (Tong et al., J. Med. Chem. (1979), 22, 912) or by reaction of the corresponding anthracyclinone compound with rhodosamine.

The linkage between an anthracyclinone obtained by biological means and the rhodosamine can also be carried out by the process of Essery and Doyle (Can. J. Chem. (1980) 58, 1869). In this reaction the rhodosaminyl radical is bonded to position 7 of the anthracyclinone.

It is already known per se that daunomycin (7-O-α-L-daunosaminyl-daunomycinone) or adriamycin (7-O-α-L-daunosaminyl-adriamycinone) are photolytically decomposed on exposure to light (Tavoloni et al., J. Pharmacol. 1980), 32, 860), whereupon the formation of polymers has been suggested (Williams & Tritton, Photochem. Photobiol. (1981), 34, 131).

On the other hand, it is known that aclacinomycin A, an anthracycline in which the trisaccharide [L-cinerulose A]-α-(1→4)-[2-deoxy-L-fucose]-α(1→4)-[α-L-rhodosamine] is bonded in position 7 of the aglycone aclavinone, also undergoes photolytic decomposition to a small extent. The decomposition products have been isolated and identified as 3'-N-monodemethylated aclacinomycin A (isolated in 3.5% yield), and 3'-N-didemethylated aclacinomycin A (isolated in 5.5% yield), using ethyl ether and chloroform as a solvent, respectively (Oki et al., J. Antibiotics (1979), 32, 801).

It was then possible, by mild acid hydrolysis, to obtain 7-O-α-L-(3'-N-methyldaunosaminyl)-aclavinone which is the only compound hitherto described of the formula I, in which $R^1$ is H, $R^2$ is OH, $R^3$ is H, $R^4$ is OH, $R^5$ is $COOCH_3$, $R^6$ is $CH_2CH_3$ and $R^7=R^8$ is H.

Furthermore, it is disclosed by Tanaka et al., J. Antibiotics (1982), 35, 312, that the anthracycline in which the abovementioned trisaccharide chain is bonded in position 7 of the aglycone daunomycinone also undergoes photolytic decomposition by sunlight. The decomposition products which have been isolated in small yields are the 3'-N-monodemethylated anthracycline (in 15% yield) and the 3'-N-didemethylated anthracycline (in 8% yield), the photolytic decomposition reaction having been carried out in chloroform as solvent.

It has now been found, surprisingly, that 7-O-α-L-rhodosaminyl-anthracyclinone compounds of the formula I in which $R^1$ to $R^4$ and $R^6$ have the said meanings, $R^5$ is hydrogen or a hydroxyl or a methoxycarbonyl group, $R^7$ is hydrogen, and $R^8$ is a methyl group, can be converted, specifically and in good yield, in contrast to the statements known from the literature, into their corresponding 3'-N-monodemethylated analogs without didemethylation being observed to any noteworthy extent.

This opens up satisfactory and straightforward access to the new class of compounds, the 7-O-(3'-N-methyl-α-L-daunosaminyl)anthracyclinones which are not accessible by the route of reductive alkylation with formaldehyde and sodium cyanoborohydride, as has been shown by the example of daunomycin and adriamycin (Tong et al., J. Med. Chem. (1979), 22, 912).

It has also been established, surprisingly, that even anthracyclines which carry in position 10 of the aglycone an α-L-rhodosaminyl radical, and in position 7 an α-L-rhodosaminyl radical in which $R^7$ is a radical of the general formula IV, can be specifically demethylated in good yield to give the corresponding anthracyclines which carry in position 10 of the aglycone a 3'-N-methyl-α-L-daunosaminyl radical.

It has also been established that anthracyclines which have the sugar residue rhodosamine both in position 7 and in position 10 of the aglycone can be specifically demethylated in good yield to give the corresponding anthracyclines which have the 3'-N-methyl-α-L-daunosamine residue both in position 7 and in position 10 of the aglycone.

Finally, it has also been established in these investigations that anthracyclines which carry the sugar rhodosamine in position 7 of the aglycone, and in which $R^5$ (in position 10 of the aglycone) is a structure of the formula III, can be specifically demethylated, likewise in good yield, to give the corresponding anthracyclines which carry the 3'-N-methyl-α-L-daunosamine residue in position 7 of the aglycone.

Furthermore, it has been found that all these 3'-N-methyldaunosaminyl-anthracyclinones obtained by photolytic demethylation of rhodosaminyl-anthracyclinones can be selectively modified or substituted on their methylamino group in a straightforward manner which is known per se, by which means many other new anthracyclines having cytostatic activity are obtained.

It has also been found, surprisingly, that photolytic demethylation of 7-O-α-L-rhodosaminyl-anthracyclinones may result, in a side reaction, in compounds of the formula I in which $R^1$ to $R^4$ and $R^6$ have the indicated meanings, $R^5$ is hydrogen or a hydroxyl or methoxycarbonyl group, $R^7$ is hydrogen, and $R^8$ is a formyl group.

Based on these findings, the process according to the invention for the preparation of the new anthracycline derivatives, having cytostatic activity, of the present invention comprises a compound of the formula I in which the substituents have the following meanings:

$R^1$ is hydrogen or a hydroxyl group,
$R^2$ is hydrogen or a hydroxyl or methoxy group,
$R^3$ is hydrogen or a hydroxyl group,
$R^4$ is hydrogen or a hydroxyl group,
$R^5$ is hydrogen, a hydroxyl or a methoxycarbonyl group, or a substituent of the general formula II in which $R^{8a}$ has the meaning indicated under $R^8$, or a structure of the formula III,
$R^6$ is ethyl, methylcarbonyl, hydroxymethylcarbonyl, hydroxyalkyl or dihydroxyalkyl,
$R^7$ is hydrogen or a substituent of the general formula IV, and
$R^8$ is a methyl group,
being subjected to (a) elimination by photolytic means of a methyl group bonded to nitrogen under the action of light in the presence of a solvent mixture composed of halogenated alkane and an alcohol, and, (b) where appropriate reaction of the 3'-N-methylamino derivative formed in stage (a) with activated acetonitrile, or, where appropriate, (c) reaction of the 3'-N-methylamino derivative formed in stage (a) with an activated acyl compound, or, where appropriate, (d) reaction of the 3'-N-methylamino derivative formed in stage (a) with an aldehyde, or, where appropriate, (e) reaction of the 3'-N-methylamino derivative formed in stage (a) with an optionally substituted aliphatic iodo, tosyl or trifluoromethanesulfonyl compound, and, where appropriate, (f) conversion of the reaction product of stage (a), (b), (c), (d) or (e) in a manner known per se into the salt of an inorganic or organic acid.

It has proved particularly advantageous, especially with regard to the yield obtained, if the photolytic elimination of the methyl group is carried out in the presence of a solvent mixture composed of 10 to 30 parts by volume of chloroform and 1 part by volume of alcohol in a concentration between 0.1 and 1 millimole per liter at a temperature between 0° C. and the boiling point of the solvent mixture under the action of strong light. Good results are also obtained by use of carbon tetrachloride in place of chloroform. Particularly good results are achieved when methyl alcohol is used as the alcohol.

It proves particularly advantageous for the photolytic demethylation reaction if the solvent mixture with the anthracycline compound contained therein has the largest possible surface area, and this can be achieved by, for example, introducing the solution into a wide-bowled vessel or falling-film apparatus and then irradiating it with sunlight or an artificial light source, preferably with the visible light from an incandescent lamp, for example a photolamp or a 500 watt emitter, from a short distance, for example of 20 to 30 cm, the light being expediently reflected by an aluminum foil to increase the photolytic yield.

In the photolytic process according to the invention, a compound of the formula I in which $R^1$ to $R^7$ have the above-mentioned meaning, and $R^8$ is hydrogen, is obtained.

The compound is isolated by removal of the solvent, and is extracted by shaking an acidic aqueous solution, for example an aqueous solution which contains hydrochloric acid and has pH 2 to 4, several times with a suitable organic solvent, for example with chloroform, and the aqueous phase is freeze-dried to isolate the corresponding acid addition compound, or the aqueous phase is neutralized or basified, for example to pH 8, with sodium bicarbonate for example, and again extracted with a suitable organic solvent, for example with chloroform, whereupon the 3'-N-methylamino compound which has formed goes into the organic phase, from which it is isolated in pure form after removal of the solvent and, where appropriate, after further purification processes which are known per se, for example after silica gel chromatography.

The compound of the formula I which has been obtained in this way and in which $R^1$ to $R^7$ have the abovementioned meanings, and $R^8$ is hydrogen, can be further derivatized on the methylamino group in a suitable manner which is known per se. This can take place by, for example, reaction of iodoacetonitrile or bromoacetonitrile in a suitable solvent, for example dimethylformamide, in the presence of a suitable base, for example triethylamine, which results in a compound of the formula I in which (a) in the case where $R^5$ in the starting compound was hydrogen or a hydroxyl or a methoxycarbonyl group, and $R^7$ was hydrogen, $R^1$ to $R^4$ and $R^6$ have the said meanings, $R^5$ is hydrogen or a hydroxyl or a methoxycarbonyl group, $R^7$ is hydrogen and $R^8$ is cyanomethyl, or (b) in the case where $R^5$ in the starting compound was an α-L-rhodosaminyl radical, and $R^7$ was hydrogen, $R^1$ to $R^4$ and $R^6$ have the said meanings, $R^5$ is a structure of the formula II with $R^{8a}$=cyanomethyl, $R^7$ is hydrogen, and $R^8$ is once again cyanomethyl, or (c) in the case where $R^5$ in the starting compound was an α-L-rhodosaminyl radical, and $R^7$ was a structure of the formula IV, $R^1$ to $R^4$ and $R^6$ have the said meanings, $R^5$ is a structure of the formula II with $R^{8a}$=cyanomethyl, $R^7$ is a structure of the formula IV, and $R^8$ is a methyl group, or (d) in the case where $R^5$ in the starting compound was a radical of the formula III, and $R^7$ was hydrogen, $R^1$ to $R^4$ and $R^6$ have the said meanings, $R^5$ is a structure of the formula III, $R^7$ is hydrogen, and $R^8$ is cyanomethyl.

Reaction with an acylating agent, for example with acetic anhydride or acetyl chloride or trifluoroacetic anhydride or the mixed anhydride of formic acid and acetic acid, in a suitable solvent, for example in methanol, results in a compound of the formula I in which, in the abovementioned cases (a) to (d), in place of the cyanomethyl group $R^8$ or $R^{8a}$ is a substituent of the general formula $COR^9$, it being possible for $R^9$ to be hydrogen, $CH_3$, $CF_3$ or $CCl_3$.

Reaction with an aliphatic or aromatic aldehyde of the formula $R^{10}CHO$, which can optionally be substituted in a suitable manner, it being necessary for the nature of the substituent to be such that it is inert toward the aldehyde group, such as, for example, methyl, ethyl, hydroxyl, methoxy, ethoxy, nitro, cyano, fluoro, chloro, or bromo, in the presence of a suitable reducing agent such as, for example, sodium cyanoborohydride, results in a compound of the formula I, in which, in the abovementioned cases (a) to (d), in place of the cyanomethyl group $R^8$ or $R^{8a}$ is a substituent of the general formula $CH_2R^{10}$, $R^{10}$ being defined by the structure of the aldehyde used.

Reaction with an aliphatic or substituted aliphatic iodo, tosyl or trifluoromethanesulfonyl compound, where appropriate with the addition of a suitable base, for example triethylamine, results in a compound of the formula I in which, in the abovementioned cases (a) to (d), in place of the cyanomethyl group $R^8$ or $R^{8a}$ is a substituent of the general formula $CH_2R^{10}$, $R^{10}$ being defined by the structure of the iodide, tosylate or trifluoromethanesulfonate used.

The new anthracycline derivatives obtained by the process according to the invention are distinguished by cytostatic activity, and hence they can be processed, together with the customary pharmaceutical manufacturing aids and/or diluents, to give pharmaceuticals for use in cancer therapy. In this connection, the methods of dosage and use essentially correspond to those for the known substances adriamycin, daunomycin, aclacinomycin, 4'-epiadriamycin, 4'-methoxyadriamycin or 4'-deoxyadriamycin.

The pharmaceuticals prepared in this way can additionally contain other active substances as long as the latter do not show undesired side effects with the compounds according to the invention.

The cytostatic activity of the compounds according to the invention have been tested using mouse L1210 leukemia cells. Use was made for this by the formation of L1210 leukemia cell colonies in agar plates. This method is used to detect the effect of the test substances on the growth behavior of the cells over 1 hour or over several generations. In this connection, with a cell cycle time of 10-12 hours, about 14 consecutive generations are observed in a 7-day duration of the test. In this test, the substances having cytostatic activity according to the invention bring about a reduction, compared with an untreated control sample, in the number of colonies which is to be observed.

Details of the test method are evident from the procedure for determining the formation of colonies given hereinafter.

Procedure for Determining the Formation of L1210 Leukemia Cell Colonies in Soft Agar 500 leukemia cells per plate were incubated with various concentrations of the test substance at 37° C. for 1 hour. These cells were then washed twice with McCoy 5A medium, 0.3% agar was added, and finally the mixture was poured into Petri dishes. Controls were incubated only with fresh medium. In place of the incubation for one hour, in some cases various concentrations and test substances were mixed with the upper agar layer in order in this way to achieve continuous exposure of the cells throughout the incubation time. After the agar had solidified, the plates were incubated in an incubator at 37° C. for 7 days (5% by volume $CO_2$, 95% relative atmospheric humidity). Thereafter the number of colonies with a diameter of more than 60 $\mu$m which had formed was counted. The results have been stated as the number of colonies in treated agar plates as a percentage of the untreated control. The dose-effect graph obtained in this way was used to determine the $IC_{50}$ as a measure of the activity of the substance. The results for the compounds described here are compiled in Table 1 which follows, comparing with adriamycin.

TABLE 1[a]

| | | | Compound of the formula I | | | | Substance No. (Example) |
|---|---|---|---|---|---|---|---|
| $R^1$ | $R^2$ | $R^5$ | $R^6$ | $R^7$ | $R^{8a}$ | $R^8$ | |
| Adriamycin | | | | | | | |
| H | OH | OH | $CH_2CH_3$ | H | — | H | (1) |
| H | OH | OH | $CH_2CH_3$ | H | — | H | (2) |
| OH | OH | OH | $CH_2CH_3$ | H | — | H | (3) |
| OH | OH | OH | $CH_2CH_3$ | H | — | H | (4) |
| OH | OH | $COOCH_3$ | $CH_2CH_3$ | H | — | H | (5) |
| H | OH | OH | $CH_2CH_3$ | H | — | CHO | (6) |
| H | OH | OH | $CH_2CH_3$ | H | — | $CH_2CN$ | (7) |
| OH | OH | OH | $CH_2CH_3$ | H | — | $CH_2CN$ | (8) |
| H | OH | OH | $CH_2CH_3$ | H | — | Benzyl | (9) |
| OH | OH | OH | $CH_2CH_3$ | H | — | Benzyl | (10) |
| H | OH | OH | $CH_2CH_3$ | H | — | $CH_2CH_3$ | (11) |
| H | OH | OH | $CH_2CH_3$ | H | — | Propyl | (12) |
| H | OH | OH | $CH_2CH_3$ | H | — | Butyl | (13) |
| OH | OH | $COOCH_3$ | $CH_2CH_3$ | H | — | $COCH_3$ | (14) |
| H | OH | II | $CH_2CH_3$ | H | H | H | (15) |
| H | OH | II | $CH_2CH_3$ | IV | H | $CH_3$ | (16) |
| H | OH | III | $CH_2CH_3$ | H | — | H | (17) |

[a]$R^3 = R^4 =$ OH applies to the compounds mentioned

| $R^1$ | $R^2$ | $R^5$ | $R^6$ | $R^{8a}$ | $R^8$ | Substance No. (Example) |
|---|---|---|---|---|---|---|
| H | OH | OH | $CH_2CH_3$ | — | Pentyl | (18) |
| H | OH | OH | $CH_2CH_3$ | — | Hexyl | (19) |
| H | OH | OH | $CH_2CH_3$ | — | Heptyl | (20) |
| H | OH | OH | $CH_2CH_3$ | — | Octyl | (21) |
| H | OH | OH | $CH_2CH_3$ | — | 4-Chlorobenzyl | (22) |
| H | OH | OH | $CH_2CH_3$ | — | 4-Bromobenzyl | (23) |
| H | OH | OH | $CH_2CH_3$ | — | 4-Nitrobenzyl | (24) |
| H | OH | OH | $CH_2CH_3$ | — | 4-Cyanobenzyl | (25) |
| H | OH | OH | $CH_2CH_3$ | — | Cyclohexylmethyl | (26) |
| OH | OH | OH | $CH_2CH_3$ | — | Pentyl | (27) |
| H | OH | II | $CH_2CH_3$ | Benzyl | Benzyl | (28) |
| H | OH | II | $CH_2CH_3$ | Pentyl | Pentyl | (29) |
| H | OH | II | $CH_2CH_3$ | Cyanomethyl | Cyanomethyl | (30) |
| H | $OCH_3$ | H | $COCH_3$ | — | H | (31) |

TABLE 1-continued

| H | OCH$_3$ | H | CHOHCH$_3$ | — | | H | (32) |
|---|---|---|---|---|---|---|---|

$^a$R$^3$ = R$^4$ = OH and R$^7$ = H applies to the said compounds

| Substance No. (Example) | RF values$^a$ Mobile phase | | | Continuous incubation IC$_{50}$ (μg/ml) | 1 h incubation IC$_{50}$ (μg/ml) |
|---|---|---|---|---|---|
| | 1 | 2 | 3 | | |
| | | | | 0.02 | 0.04 |
| (1) | 0.86 | 0.60 | 0.29 | 0.02 | 0.038 |
| (2) | 0.86 | 0.60 | | 0.02 | 0.026 |
| (3) | 0.78 | 0.48 | | 0.11 | 0.13 |
| (4) | 0.78 | 0.48 | 0.1 | 0.11 | 0.13 |
| (5) | 0.87 | 0.20 | 0.13 | 0.28 | >1 |
| (6) | 0.88 | 0.65 | 0.66 | 0.044 | 0.15 |
| (7) | 0.82 | 0.68 | 0.53 | 0.013 | 0.021 |
| (8) | 0.83 | 0.69 | 0.48 | 0.042 | 0.2 |
| (9) | 0.78 | 0.50 | 0.46 | 0.028 | 0.32 |
| (10) | 0.78 | 0.49 | 0.45 | | |
| (11) | 0.53 | 0.30 | 0.09 | 0.007 | 0.08 |
| (12) | 0.65 | 0.38 | 0.18 | 0.026 | 0.1 |
| (13) | 0.75 | 0.45 | 0.29 | 0.018 | 0.125 |
| (14) | | | | 0.5 | >1 |
| (15) | 0.43 | 0.20 | 0.13 | >1 | >1 |
| (16) | 0.52$^b$ | | | 0.0033 | 0.025 |
| (17) | 0.38$^b$ | | | 0.0024 | 0.06 |
| (18) | 0.78 | 0.52 | 0.30 | 0.075 | 0.48 |
| (19) | 0.81 | 0.59 | 0.32 | 0.13 | 1.2 |
| (20) | 0.68 | 0.48 | 0.31 | 0.38 | 1.9 |
| (21) | 0.65 | 0.49 | 0.28 | 0.46 | 2.8 |
| (22) | 0.67 | 0.41 | 0.61 | 0.026 | 0.95 |
| (23) | 0.74 | 0.47 | 0.70 | 0.08 | >1 |
| (24) | 0.69 | 0.52 | 0.83 | 0.16 | 2.5 |
| (25) | 0.66 | 0.49 | 0.81 | 0.11 | >1 |
| (26) | 0.73 | 0.48 | 0.39 | | |
| (27) | 0.68 | 0.45 | 0.20 | 0.06 | >1 |
| (28) | 0.60 | 0.40 | 0.40 | 0.0065 | 0.12 |
| (29) | 0.57 | 0.36 | 0.08 | 0.1 | 0.6 |
| (30) | 0.79 | 0.68 | 0.51 | | |
| (31) | 0.50 | 0.29 | 0.01 | | |
| (32) | 0.35 | 0.16 | 0.009 | 0.5 | 1.3 |

Notes on Table 1
$^a$R$^3$ = R$^4$ = OH and R$^7$ = H applies to the said compounds
$^a$Mobile phase 1: chloroform/methanol/acetic acid/water/triethylamine (80/20/10/4/0.2)
Mobile phase 2: mobile phase 1/dichloromethane (2/1)
Mobile phase 3: dichloromethane/methanol (9/1)
$^b$Chloroform/methanol/acetic acid/water (8/1/1/0.2)
The stated numbers are ratios by volume.

The preparation process according to the invention is illustrated by Examples 1 to 32 which are detailed hereinafter and in which preferred compounds according to the invention have been prepared by the claimed process.

The structure of the prepared compounds was determined using $^1$H and $^{13}$C NMR and MS spectroscopy. The reactions were followed, and the resulting compounds were examined, by thin-layer chromatography or using HPLC techniques.

Unless otherwise noted, thin-layer chromatography was carried out on precoated silica gel plates in mobile phase 1: methanol (20 parts)/chloroform (80 parts)/acetic acid (10 parts)/water (4 parts)/triethylamine (0.2 parts). Unless otherwise noted, column chromatography was carried out on silica gel 60 of diameter 20–45 μm or 0.063–0.200 mm. The abovementioned parts are parts by volume. The yields have not been optimized.

EXAMPLE 1

7-O-(3'-N-Methyl-α-L-daunosaminyl)-β-rhodomycinone (compound 1)

(Compound of the formula I with R$^1$=H, R$^2$=R$^3$=R$^4$=R$^5$=OH, R$^6$=CH$_2$CH$_3$ and R$^7$=R$^8$=H)

A solution of 500 mg=0.92 mmol of 7-O-α-L-rhodosaminyl-β-rhodomycinone, which had been obtained by known processes, for example Yoshimoto et al., J. Antibiot. (1984) 37, 920, in a mixture of chloroform (1200 ml) and methanol (50 ml) was distributed over 8 Petri dishes of diameter 19 cm and irradiated on a reflecting underlay for 5 hours with two 500 watt emitters, stirring gently, at a distance of about 25 cm, following the reaction by thin-layer chromatography.

The solutions were then combined, and the solvent was removed in a rotary evaporator. The residue was dissolved in the minimum amount of methanol, water was added, the pH was adjusted to 4 with 1% hydrochloric acid, and the mixture was extracted several times with chloroform, during which the desired product remained in the aqueous phase. This "chloroform phase I" was concentrated and further processed as described in Example 6. The aqueous phase was adjusted to pH 7–8 with a saturated aqueous solution of sodium bicarbonate, and the desired product was extracted with chloroform.

Yield: 264 mg (0.50 mmol)=54%.

EXAMPLE 2

7-O-(3'-N-Methyl-α-L-daunosaminyl)-β-rhodomycinone hydrochloride (compound 2)

(HCl adduct of a compound of the formula I with $R^1=H$, $R^2=R^3=R^4=R^5=OH$, $R^6=CH_2CH_3$ and $R^7=R^8=H$)

500 mg of 7-O-α-L-rhodosaminyl-β-rhodomycinone were demethylated and worked up in analogy to Example 1. The aqueous solution which had been adjusted to pH 4 with 1% hydrochloric acid was extracted several times with chloroform and then freeze-dried.

Yield: 282 mg (0.50 mmol)=54%.

EXAMPLE 3

7-O-(3'-N-Methyl-α-L-daunosaminyl)-β-isorhodomycinone (compound 3)

(Compound of the formula I with $R^1=R^2=R^3=R^4=R^5=OH$, $R^6=CH_2CH_3$ and $R^7=R^8=H$)

280 mg (0.50 mmol) of 7-O-α-L-rhodosaminyl-β-isorhodomycinone, which had been obtained by mild acid hydrolysis of beta-isorhodomycin II which is known from the literature (Brockmann et al., Tetrahedron Letters 1969, 415) in analogy to the preparation of 7-O-α-L-rhodosaminyl-β-rhodomycinone from β-rhodomycin II, were dissolved in 60 ml of methanol, 1000 ml of chloroform were added, and the solution was irradiated as in Example 1 for 90 minutes. The solvent was then removed in a rotary evaporator, the residue was taken up in a little methanol, the pH was adjusted to 1 with 1% hydrochloric acid, and the mixture was diluted to about 400 ml with water and extracted several times with chloroform, during which the desired product remained in the aqueous phase. Finally, the pH was adjusted to 7 with a saturated aqueous solution of sodium bicarbonate, and the desired product was extracted with chloroform.

Yield: 234 mg (0.43 mmol)=86%.

It is possible, if necessary, to purify the product by chromatography on a silica gel 60 column in the mobile phase dichloromethane/methanol (4/1).

EXAMPLE 4

7-O-(3'-N-Methyl-α-L-daunosaminyl)-β-isorhodomycinone hydrochloride (compound 4)

(HCl adduct of a compound of the formula I with $R^1=R^2=R^3=R^4=R^5=OH$, $R^6=CH_2CH_3$ and $R^7=R^8=H$)

50 mg (0.09 mmol) of 7-O-α-L-rhodosaminyl-β-isorhodomycinone were demethylated and worked up in analogy to Example 3. The aqueous solution which had been acidified with 1% hydrochloric acid was extracted several times with chloroform and then freeze-dried.

Yield: 41 mg (0.07 mmol)=78%.

EXAMPLE 5

7-O-(3'-N-Methyl-α-L-daunosaminyl)-ε-isorhodomycinone (compound 5)

(Compound of the formula I with $R^1=R^2=R^3=R^4=OH$, $R^5=COOCH_3$, $R^6=CH_2CH_3$ and $R^7=R^8=H$)

62 mg (0.10 mmol) of 7-O-α-L-rhodosaminyl-ε-isorhodomycinone were demethylated in analogy to Example 1, and the reaction was followed by thin-layer chromatography. Once the starting compound had been consumed, the solvent was removed in a rotary evaporator, and the reaction product was subjected to repeated column chromatography (10 g of silica gel 60 for HPLC, 25–40 μm, Merck; mobile phase: dichloromethane/methanol/water (80/8/1)). Residues of silica gel were removed by extracting the purified solid product several times with chloroform and recovering it from the combined chloroform phase.

Yield: 27 mg (not optimized).

The molecular peak in the FAB mass spectrum (M+H+ =588) is consistent with the calculated molecular mass of 587.6 ($C_{29}H_{33}NO_{12}$).

EXAMPLE 6

7-O-(3'-N-Formyl-3'-N-methyl-α-L-daunosaminyl)-β-rhodomycinone (compound 6)

(Compound of the formula I with $R^1=H$, $R^2=R^3=R^4=R^5=OH$, $R^6=CH_2CH_3$, $R^7=H$ and $R^8=CHO$)

Various product mixtures of "chloroform phase I" obtained in analogy to Example 1 were combined (390 mg) and separated on a silica gel column (diameter 3.5 cm, packed height 10 cm; mobile phase: dichloromethane/methanol (19/1)) under slight pressure (with the aid of compressed air). The fractions containing pure substance of $R_f$ 0.29 in dichloromethane/methanol (19/1) were collected.

Yield: 80 mg.

The molecular peak in the FAB mass spectrum (M+H+ =558) is consistent with the calculated molecular mass of 557.5 ($C_{28}H_{31}NO_{11}$).

EXAMPLE 7

7-O-(3'-N-Cyanomethyl-3'-N-methyl-α-L-daunosaminyl)-β-rhodomycinone (compound 7)

(Compound of the formula I with $R^1=H$, $R^2=R^3=R^4=R^5=OH$, $R^6=CH_2CH_3$, $R^7=H$ and $R^8=CH_2CN$)

630 mg (3.8 mmol=10 equivalents) of iodoacetonitrile were added to a solution of 7-O-(3'-N-methyl-α-L-daunosaminyl)-β-rhodomycinone (200 mg=0.38 mmol) and triethylamine (1.14 mmol) in 10 ml of dry dimethylformamide, and the mixture was stirred at room temperature overnight. It was then concentrated in a rotary evaporator. The residue was taken up in chloroform, and the solution was extracted three times with water, dried with sodium sulfate and filtered, and the solvent was removed. The residue was separated on a silica gel column using dichloromethane/methanol (95/5) ($R_f$ 0.28).

Yield: 105 mg (0.18 mmol)=47%.

EXAMPLE 8

7-O-(3'-N-Cyanomethyl-3'-N-methyl-α-L-daunosaminyl)-β-isorhodomycinone (compound 8)

(Compound of the formula I with $R^1=R^2=R^3=R^4=R^5=OH$, $R^6=CH_2CH_3$, $R^7=H$ and $R^8=CH_2CN$)

30 mg of 7-O-(3'-N-methyl-α-L-daunosaminyl)-β-isorhodomycinone were reacted with iodoacetonitrile, and worked up, in analogy to Example 7, purifying on a silica gel 60 column using dichloromethane/methanol (99/1) as mobile phase.

Yield: 8 mg.

EXAMPLE 9

7-O-(3'-N-Benzyl-3'-N-methyl-α-L-daunosaminyl)-β-rhodomycinone (compound 9)

(Compound of the formula I with $R^1=H$, $R^2=R^3=R^4=R^5=OH$, $R^6=CH_2CH_3$, $R^7=H$ and $R^8=$benzyl)

6 μl (0.1 mmol) of glacial acetic acid were added to a solution of 52 mg (0.09 mmol) of 7-O-(3'-N-methyl-α-L-daunosaminyl)-β-rhodomycinone and 190 μl (1.8 mmol=20 equivalents) of benzaldehyde in 3 ml of acetonitrile/water (3/1). After 4 h, a solution of 20 mg (0.6 mmol) of sodium cyanoborohydride in 900 μl of acetonitrile/water (3/1) was added, and the mixture was subsequently stirred in the dark for 3 days. Then 15 ml of water were added, and the solution was extracted by shaking three times with 20 ml of chloroform each time. The combined chloroform phases were back-extracted successively with water and saturated sodium bicarbonate solution, the solvent was removed in vacuo, and the resulting product was chromatographed on a silica gel 60 column using dichloromethane/methanol (99/1) as mobile phase.

Yield: 30 mg (0.05 mmol)=56%.

EXAMPLE 10

7-O-(3'-N-Benzyl-3'-N-methyl-α-L-daunosaminyl)-β-isorhodomycinone (compound 10)

(Compound of the formula I with $R^1=R^2=R^3=R^4=R^5=OH$, $R^6=CH_2CH_3$, $R^7=H$ and $R^8=$benzyl)

30 mg of 7-O-(3'-N-methyl-α-L-daunosaminyl)-β-isorhodomycinone were reacted with benzaldehyde, and worked up and purified on a silica gel column using dichloromethane/methanol (99/1) as mobile phase, in analogy to Example 9.

Yield: 5 mg.

EXAMPLE 11

7-O-(3'-N-Ethyl-3'-N-methyl-α-L-daunosaminyl)-β-rhodomycinone (compound 11)

(Compound of the formula I with $R^1=H$, $R^2=R^3=R^4=R^5=OH$, $R^6=CH_2CH_3$, $R^7=H$ and $R^8=CH_2CH_3$)

52 mg of 7-O-(3'-N-methyl-α-L-daunosaminyl)-β-rhodomycinone were reacted with acetaldehyde, and worked up, in analogy to Example 9, purifying on a silica gel column using a (99/1) to (8/2) dichloromethane/methanol gradient as mobile phase.

Yield: 14 mg.

EXAMPLE 12

7-O-(3'-N-Methyl-3'-N-propyl-α-L-daunosaminyl)-β-rhodomycinone (compound 12)

(Compound of the formula I with $R^1=H$, $R^2=R^3=R^4=R^5=OH$, $R^6=CH_2CH_3$, $R^7=H$ and $R^8=$propyl)

52 mg of 7-O-(3'-N-methyl-α-L-daunosaminyl)-β-rhodomycinone were reacted with propionaldehyde, and worked up, in analogy to Example 9, purifying on a silica gel column using a (99/1) to (9/1) dichloromethane/methanol gradient as mobile phase.

Yield: 18 mg.

EXAMPLE 13

7-O-(3'-N-Butyl-3'-N-methyl-α-L-daunosaminyl)-β-rhodomycinone (compound 13)

(Compound of the formula I with $R^1=H$, $R^2=R^3=R^4=R^5=OH$, $R^6=CH_2CH_3$, $R^7=H$ and $R^8=$butyl)

52 mg of 7-O-(3'-N-methyl-α-L-daunosaminyl)-β-rhodomycynone were reacted with butyraldehyde, and worked up, in analogy to Example 9, purifying on a silica gel column using a (99/1) to (9/1) dichloromethane/methanol gradient as mobile phase.

Yield: 20 mg.

EXAMPLE 14

7-O-(3'-N-Acetyl-3'-N-methyl-α-L-daunosaminyl)-ε-isorhodomycinone (compound 14)

(Compound of the formula I with $R^1=R^2=R^3=R^4=OH$, $R^5=COOCH_3$, $R^6=CH_2CH_3$, $R^7=H$ and $R^8=COCH_3$)

15 mg of 7-O-(3'-N-methyl-α-L-daunosaminyl)-ε-isorhodomycinone were N-acetylated with 100 μl of acetic anhydride in 3 ml of methanol. The mixture was then concentrated in a rotary evaporator, the residue was taken up in saturated sodium bicarbonate solution, and the reaction product was extracted with chloroform.

Yield: 11 mg.

EXAMPLE 15

7,10-O-bis-(3'-N-Methyl-α-L-daunosaminyl)-β-rhodomycinone (compound 15)

(Compound of the formula I with $R^1=H$, $R^2=R^3=R^4=OH$, $R^5=$structure of the formula II with $R^{8a}=H$, $R^6=CH_2CH_3$ and $R^7=R^8=H$)

120 mg of 7,10-O-bis-α-L-rhodosaminyl-β-rhodomycinone (Australian Patent Application No. 84/30823) were irradiated for 3 hours in analogy to Example 1. The solvent was then removed in a rotary evaporator. The residue was taken up in a little methanol, water was added, and the mixture was extracted with chloroform at pH 2, 4, 6 and 8 successively. The product in the chloroform extracts obtained at pH 6 and 8 was chromatographed on a silica gel column using mobile phase 1 to which dichloromethane had been added in the ratio 1:1, and, after renewed extraction by shaking with aqueous sodium bicarbonate/chloroform, was isolated in pure form.

Yield: 66 mg.

EXAMPLE 16

Monodemethylated cytorhodin S (compound 16)

(Compound of the formula I with $R^1=H$, $R^2=R^3=R^4=OH$, $R^5=$structure of the formula II with $R^{8a}=H$, $R^6=CH_2CH_3$, $R^7=$structure of the formula IV, and $R^8=CH_3$)

400 mg (0.425 mmol) of cytorhodin S (as claimed in AU No. 84/30823) were photolyzed in analogy to Example 1. Alternatively, the solution was placed in a Duran 50 glass photolysis apparatus with a cooling jacket and immersion tube. Irradiation was carried out with an immersion lamp for a period of 3 hours, following the course of the reaction by thin-layer chromatography. Once the reaction was complete, the solvent was removed from the substance, which was then dried. 100 mg of reaction product were separated on 18 g of silica gel using the mobile phase mixture chloroform/methanol/99% acetic acid/water=8/1/1/0.2.

Yield: 47.5 mg.

EXAMPLE 17

Monodemethylated cytorhodin T (compound 17)

(Compound of the formula I with $R^1=H$, $R^2=R^3=R^4=OH$, $R^5=$structure of the formula III, $R^6=CH_2CH_3$ and $R^7$ and $R^8=H$)

Cytorhodin T (as claimed in AU No. 84/30823) was photolyzed in analogy to Example 1. Alternatively, 50 mg (0.053 mmol) of cytorhodin T were taken up in 5 ml of chloroform, and the solution was left to stand exposed to daylight at room temperature. The reaction was followed by thin-layer chromatography. After 7 days the solvent was removed, and the residue was purified by preparative thin-layer chromatography in the system: chloroform/methanol/99% acetic acid/water=8/1/1/0.2.

Yield: 16 mg.

EXAMPLE 18

7-O-(3'-N-Methyl-3'-N-pentyl-α-L-daunosaminyl)-β-rhodomycinone (compound 18)

(Compound of the formula I with $R^1=H$, $R^2=R^3=R^4=R^5=OH$, $R^6=CH_2CH_3$, $R^7=H$ and $R^8=$pentyl)

52 mg of 7-O-(3'-N-methyl-α-L-daunosaminyl)-β-rhodomycinone were reacted with pentanal, and worked up, in analogy to Example 9, purifying on a silica gel column in the mobile phase dichloromethane/methanol (95/5).

Yield: 25 mg (48%).

EXAMPLE 19

7-O-(3'-N-Hexyl-3'-N-methyl-α-L-daunosaminyl)-β-rhodomycinone (compound 19)

(Compound of the formula I with $R^1=H$, $R^2=R^3=R^4=R^5=OH$, $R^6=CH_2CH_3$, $R^7=H$ and $R^8=$hexyl)

52 mg of 7-O-(3'-N-methyl-α-L-daunosaminyl)-β-rhodomycinone were reacted with hexanal, and worked up, in analogy to Example 9, purifying on a silica gel column in the mobile phase dichloromethane/methanol (9/1).

Yield: 25 mg (48%).

EXAMPLE 20

7-O-(3'-N-Heptyl-3'-N-methyl-α-L-daunosaminyl)-β-rhodomycinone (compound 20)

(Compound of the formula I with $R^1=H$, $R^2=R^3=R^4=R^5=OH$, $R^6=CH_2CH_3$, $R^7=H$ and $R^8=$heptyl)

58 mg of 7-O-(3'-N-methyl-α-L-daunosaminyl)-β-rhodomycinone were reacted with heptanal, and worked up, in analogy to Example 9, purifying on a silica gel column in the mobile phase dichloromethane/methanol (9/1).

Yield: 34 mg (59%).

EXAMPLE 21

7-O-(3'-N-Octyl-3'-N-methyl-α-L-daunosaminyl)-β-rhodomycinone (compound 21)

(Compound of the formula I with $R^1=H$, $R^2=R^3=R^4=R^5=OH$, $R^6=CH_2CH_3$, $R^7=H$ and $R^8=$octyl)

58 mg of 7-O-(3'-N-methyl-α-L-daunosaminyl)-β-rhodomycinone were reacted with octanal, and worked up, in analogy to Example 9, purifying on a silica gel column in the mobile phase dichloromethane/methanol (9/1).

Yield: 40 mg (69%).

EXAMPLE 22

7-O-(3'-N-(4-Chlorobenzyl)-3'-N-methyl-α-L-daunosaminyl)-β-rhodomycinone (compound 22)

(Compound of the formula I with $R^1=H$, $R^2=R^3=R^4=R^5=OH$, $R^6=CH_2CH_3$, $R^7=H$ and $R^8=$4-chlorobenzyl)

52 mg of 7-O-(3'-N-methyl-α-L-daunosaminyl)-β-rhodomycinone were reacted with 4-chlorobenzaldehyde, and worked up, in analogy to Example 9, purifying on a silica gel column in the mobile phase dichloromethane/methanol (975/25).

Yield: 31 mg (60%).

EXAMPLE 23

7-O-(3'-N-(4-Bromobenzyl)-3'-N-methyl-α-L-daunosaminyl)-β-rhodomycinone (compound 23)

(Compound of the formula I with $R^1=H$, $R^2=R^3=R^4=R^5=OH$, $R^6=CH_2CH_3$, $R^7=H$ and $R^8=$4-bromobenzyl)

52 mg of 7-O-(3'-N-methyl-α-L-daunosaminyl)-β-rhodomycinone were reacted with 4-bromobenzaldehyde, and worked up, in analogy to Example 9, purifying on a silica gel column in the mobile phase dichloromethane/methanol (95/5).

Yield: 30 mg (58%).

EXAMPLE 24

7-O-(3'-N-(4-Nitrobenzyl)-3'-N-methyl-α-L-daunosaminyl)-β-rhodomycinone (compound 24)

(Compound of the formula I with $R^1=H$, $R^2=R^3=R^4=R^5=OH$, $R^6=CH_2CH_3$, $R^7=H$ and $R^8=$4-nitrobenzyl)

58 mg of 7-O-(3'-N-methyl-α-L-daunosaminyl)-β-rhodomycinone were reacted with 4-nitrobenzaldehyde, and worked up, in analogy to Example 9, purifying on a silica gel column in the mobile phase toluene/ethanol (965/35).

Yield: 30 mg (52%).

EXAMPLE 25

7-O-(3'-N-(4-Cyanobenzyl)-3'-N-methyl-α-L-daunosaminyl)-β-rhodomycinone (compound 25)

(Compound of the formula I with $R^1=H$, $R^2=R^3=R^4=R^5=OH$, $R^6=CH_2CH_3$, $R^7=H$ and $R^8=$4-cyanobenzyl)

58 mg of 7-O-(3'-N-methyl-α-L-daunosaminyl)-β-rhodomycinone were reacted with 4-cyanobenzaldehyde, and worked up, in analogy to Example 9, purifying on a silica gel column in the mobile phase dichloromethane/methanol (975/25).

Yield: 49 mg (84%).

EXAMPLE 26

7-O-(3'-N-Cyclohexylmethyl-3'-N-methyl-α-L-daunosaminyl)-β-rhodomycinone (compound 26)

(Compound of the formula I with $R^1$=H, $R^2$=$R^3$=$R^4$=$R^5$=OH, $R^6$=$CH_2CH_3$, $R^7$=H and $R^8$=cyclohexylmethyl)

20 mg of 7-O-(3'-N-methyl-α-L-daunosaminyl)-β-rhodomycinone were stirred at room temperature with 170 mg of cyclohexanecarbaldehyde (184 μl=40 equivalents) in the presence of 4.6 μl of acetic acid and in a solvent mixture composned of acetonitrile/water (4/1) for 10 min. Then a further 4.6 μl of acetic acid were added, and the reaction was stirred further until the starting compound had disappeared. The reaction solution was then poured into 0.1N hydrochloric acid, washing twice with n-hexane, the aqueous phase was adjusted to pH 11 with solid sodium bicarbonate, and the reaction product was extracted with chloroform and purified on a silica gel column in a mobile phase composed of mobile phase 1 and dichloromethane in the mixture ½. Residual acetic acid was removed by renewed extraction by shaking with chloroform/sodium bicarbonate solution.

Yield: 11 mg (47%).

EXAMPLE 27

7-O-(3'-N-Methyl-3'-N-pentyl-α-L-daunosaminyl)-β-isorhodomycinone (compound 27)

(Compound of the formula I with $R^1$=$R^2$=$R^3$=$R^4$=$R^5$=OH, $R^6$=$CH_2CH_3$, $R^7$=H and $R^8$=pentyl)

20 mg of 7-O-(3'-N-methyl-α-L-daunosaminyl)-β-isorhodomycinone were reacted with pentanal, and worked up, in analogy to Example 9, purifying on a silica gel column in the mobile phase dichloromethane/methanol (9/1).

Yield: 6 mg (30%).

EXAMPLE 28

7,10-O-bis-(3'-N-Benzyl-3'-N-methyl-α-L-daunosaminyl)-β-rhodomycinone (compound 28)

(Compound of the formula I with $R^1$=H, $R^2$=$R^3$=$R^4$=OH, $R^5$=structure of the formula II with $R^{8a}$=benzyl, $R^6$=$CH_2CH_3$, $R^7$=H and $R^8$=benzyl)

122 mg (0.18 mmol) of 7,10-O-bis-(3'-N-methyl-α-L-daunosaminyl)-β-rhodomycinone (compound 15) were stirred with 1.01 g (9.5 mmol) of benzaldehyde in the presence of 22 mg of acetic acid and 288 mg of sodium cyanoborohydride in acetonitrile/water (3/1) (8 ml) overnight. Then 40 ml of water were added, the pH was adjusted to 1 with hydrochloric acid, and the mixture was washed with chloroform. The aqueous phase was adjusted to pH 8 with saturated sodium bicarbonate solution and was extracted with chloroform. The extracted product mixture (110 mg) was fractionated on a 20 g silica gel column using mobile phase 1/dichloromethane (1/1) (yield: 24 mg), and then purified on a 5 g silica gel column using dichloromethane/methanol (20/1) as mobile phase.

Yield: 13 mg.

EXAMPLE 29

7,10-O-bis-(3'-N-Methyl-3'-N-pentyl-α-L-daunosaminyl)-β-rhodomycinone (compound 29)

(Compound of the formula I with $R^1$=H, $R^2$=$R^3$=$R^4$=OH, $R^5$=structure of the formula II with $R^{8a}$=pentyl, $R^6$=$CH_2CH_3$, $R^7$=H and $R^8$=pentyl)

61 mg (0.09 mmol) of 7,10-O-bis-(3'-N-methyl-α-L-daunosaminyl)-β-rhodomycinone (compound 15) were reacted with 288 mg (3.34 mmol) of valeraldehyde in the presence of 11 mg of acetic acid and 144 mg of sodium cyanoborohydride in acetonitrile/water (3/1) (3 ml) in analogy to Example 28. After 1 h, 50 ml of water were added, and the mixture was extracted several times with chloroform. The extracted product mixture was fractionated on a 10 g silica gel column using mobile phase 2, and the desired product was extracted by shaking with dichloromethane against an aqueous solution of sodium bicarbonate.

Yield: 27 mg (37%).

EXAMPLE 30

7,10-O-bis-(3'-N-Cyanomethyl-3'-N-methyl-α-L-daunosaminyl)-β-rhodomycinone (compound 30)

(Compound of the formula I with $R^1$=H, $R^2$=$R^3$=$R^4$=OH, $R^5$=structure of the formula II with $R^{8a}$=cyanomethyl, $R^6$=$CH_2CH_3$, $R^7$=H and $R^8$=cyanomethyl)

Reaction of 84 mg (0.125 mmol) of 7,10-O-bis-(3'-N-methyl-α-L-daunosaminyl)-β-rhodomycinone (compound 15) and 175 μl (2.5 mmol) of iodoacetonitrile in dry dimethylformamide (5 ml) in the presence of 400 μl of triethylamine, and working up were carried out in analogy to Example 7. The product mixture was eluted through a 30 g silica gel column, initially with chloroform and subsequently with a chloroform/methanol mixture (9/1).

Yield: 49 mg (52%).

EXAMPLE 31

3'-N-Methyldaunomycin (compound 31)

(Compound of the formula I with $R^1$=H, $R^2$=$OCH_3$, $R^3$=$R^4$=OH, $R^5$=H, $R^6$=$COCH_3$ and $R^7$=$R^8$=H)

Demethylation of 95 mg (0.17 mmol) of N,N-dimethyldaunomycin (Tong et al., J. Med. Chem. (1979), 22, 912) and working up were carried out in analogy to Example 1.

Yield: 29 mg (31%).

EXAMPLE 32

3'-N-Methyl-13-dihydrodaunorubicin (compound 32)

(Compound of the formula I with $R^1$=H, $R^2$=$OCH_3$, $R^3$=$R^4$=OH, $R^5$=H, $R^6$=$CHOHCH_3$ and $R^7$=$R^8$=H)

Demethylation of 50 mg (0.09 mmol) of N,N-dimethyl-13-dihydrodaunorubicin (Tong et al., J. Med. Chem. (1979), 22, 912) and working up was carried out in analogy to Example 1.

Yield: 6.5 mg (13%).

Table 2 which follows is a compilation of the NMR data of the new compounds 1 to 17 which are described above, and Table 3 is a compilation of the NMR data of the new compounds 18-32 which are described above.

TABLE 2

400 MHz $^1$H NMR data of various compounds of the formula I
The substance numbers in the first line correspond to the relevant example numbers; the indices (a) to (u) serve for more detailed characterization:

abbreviations  s: singlet
d: doublet
t: triplet
q: quartet
dd: doublet of doublets
bs: broad singlet (a) Spectrum measured in CDCl$_3$/D$_6$-DMSO with TMS as 7.35
(b) 300 MHz spectrum
(c) Spectrum measured in CDCl$_3$ with TMS as reference
(d) Isolated signals are observed for the two rotamers
(e) CHO: 8.12 s; 8.01 s
(f) NCH$_2$CN: 3.59 dd
(g) NCH$_2$Ph: β: 3.62 d; α: 3.40 d
(h) Value in CD$_3$OD
(i) Not unambiguously identifiable
(k) Assignment of the OH groups ambiguous
(l) Data taken from another spectrum
(m) 270 MHz spectrum; COOCH$_3$: 3.72 s
(n) NCOCH$_3$: 2.04 s
   COOCH$_3$: 3.71 s
(o) NCH$_2$CN: 3.60 dd
(p) Butyl CH$_3$: 0.87 t
(q) NCH$_2$Ph: β: 3.66 d; α: 3.45 d
(r) N-Ethyl CH$_3$: 1.04 t
(s) N-Propyl CH$_3$: 0.84 t
(t) Do not appear under the measurement conditions
(u) 270 MHz spectrum, measured with addition of D$_2$O and Na$_2$CO$_3$

| Substance No. Proton | 1[a] | 2[a] | 4[a] | 5[m] |
|---|---|---|---|---|
| H-1 | 7.90 d | 7.87 d | — | — |
| H-2 | 7.73 t | 7.79 t | 7.35 s | 7.30 s |
| H-3 | 7.35 d | 7.5 d | | |
| H-7 | 5.12 m | 5.00 d | 5.01 d | 5.25 d |
| H-8α | 2.20 m | 1.9-2.2 m | 1.85-2.14 m | |
| H-8β | | 2.18 dd | 2.19 dd | |
| H-10 | 4.81 s | 4.72 s | 4.73 s | 4.28 s |
| H-13α | 1.7-2.0 m | 1.70 m | 1.69 m | |
| H-13β | | 1.76 m | 1.77 m | |
| H$_3$-14 | 1.10 t | 1.05 t | 1.06 t | 1.13 t |
| H-1' | 5.43 bs | 5.43 bs | 5.44 d | 5.49 d |
| H$_2$-2' | 1.7-2.0 m | 1.9-2.2 m | 1.85-2.14 m | |
| H-3' | 2.67 m | 3.49 m[h] | i | 2.81 bd |
| H-4' | 3.88 bs | 3.86 bs | 3.86 bs | |
| H-5' | 4.10 q | 4.18 q | 4.18 q | 4.10 q |
| H$_3$-6' | 1.35 d | 1.27 d | 1.28 d | 1.37 d |
| B—CH$_3$ | 2.33 s | 2.51 s | 2.52 t | 2.39 bs |
| OH-1 | — | — | | 12.28 s |
| OH-4 | — | 12.12 bs[l] | | |
| OH-6 | — | 12.88 bs[l] | 12.99[k] | |
| OH-11 | — | 13.69 bs[l] | 13.03[k] | |
| OH-9 | 3.85 s | 3.63 s | 3.84 s | |

| Substance No. Proton | 6[c,d,e] | 7[c,f] | 8[c,o] | 9[c,g] |
|---|---|---|---|---|
| H-1 | 7.88 d; 7.85 d | 7.88 dd | — | 7.87 dd |
| H-2 | 7.72 t; 7.69 t | 7.71 t | 7.28 s | 7.71 t |
| H-3 | 7.33 d; 7.27 d | 7.31 dd | | 7.32 dd |
| H-7 | 5.15 m; 5.12 m | 5.14 m | 5.13 m | 5.17 m |
| H-8α | 2.0-2.6 m | 2.12 dd | 2.12 dd | 2.13 dd |
| H-8β | | 2.25 d | 2.25 d | 2.28 d |
| H-10 | 4.92 d; 4.90 d | 4.94 d | 4.94 s | 4.92 s |
| H-13α | 1.76 m | 1.77 m | 1.77 m | 1.79 m |
| H-13β | 1.86 m | 1.79-1.94 m | 1.80-1.94 m | 1.87 m |
| H$_3$-14 | 1.12 t | 1.12 t | 1.13 t | 1.14 t |
| H-1' | 5.55 s; 5.54 s | 5.52 d | 5.52 d | 5.54 bs |
| H$_2$-2' | 2.0-2.6 m | 1.79-1.94 m | 1.80-1.94 m | 1.91 m |
| H-3' | 3.56 bd; 2.0-2.6 m | 2.66 m | 2.68 m | 2.60 dt |
| H-4' | 3.86 d; 3.70 d | 3.70 bs | 3.71 bs | 3.82 bs |
| H-5' | 4.4 q; 4.2 q | 4.16 q | 4.17 q | 4.13 q |
| H$_3$-6' | 1.32 d; 1.30 d | 1.39 d | 1.39 d | 1.43 d |
| N—CH$_3$ | 3.00 s; 2.92 s | 2.42 s | 2.42 s | 2.09 s |
| OH-1 | — | — | 12.26 bs | — |
| OH-4 | 2.08 s; 12.06 s | 12.10 s | | 12.11 bs |
| OH-6 | 12.85 s; 12.82 s | 12.85 s | 12.87 bs | 12.82 bs |
| OH-11 | 13.58 s; 13.52 s | 13.59 s | 12.93 bs | 13.62 bs |
| OH-9 | 3.75 s; 3.66 s | 3.77 s | 3.78 s | |

| Substance No. Proton | 10[c,q] | 11[c,r] | 12[c,s] | 13[c,p] |
|---|---|---|---|---|
| H-1 | | 7.87 dd | 7.87 dd | 7.88 dd |
| H-2 | | 7.71 t | 7.71 t | 7.71 t |
| H-3 | | 7.32 dd | 7.31 dd | 7.32 dd |
| H-7 | 5.19 m | 5.15 m | 5.14 m | 5.15 m |
| H-8α | (i) | 2.12 dd | 2.12 dd | 2.12 dd |
| H-8β | 2.28 | 2.25 d | 2.25 d | 2.25 d |
| H-10 | 4.93 | 4.90 d | 4.90 s | 4.91 s |
| H-13α | (i) | 1.7-1.93 m | 1.7-2.0 m | 1.7-2.0 m |
| H$_3$-14 | 1.13 t | 1.12 t | 1.12 t | 1.12 t |
| H—β | | | | |
| H-1' | 5.55 bs | 5.53 bd | 5.52 bd | 5.52 d |
| H-2' | (i) | (i) | (i) | 1.7-2.0 m |
| H-3' | 2.65 m | 2.6-2.8 m | 2.59 m | (i) |
| H-4' | 3.84 bs | 3.81 bs | 3.77 bs | 3.76 bs |
| H-5' | 4.12 q | 4.09 q | 4.09 q | 4.09 q |
| H$_3$-6' | 1.43 d | 1.39 d | 1.40 d | 1.40 d |
| N—CH$_3$ | 2.13 s | 2.34 s | 2.29 s | 2.29 s |
| OH-1 | 12.35 bs | — | — | — |
| OH-4 | | (t) | (t) | 12.12 bs |
| OH-6 | 12.98 bs | (t) | (t) | 12.82 bs |
| OH-11 | | (t) | (t) | 13.58 bs |
| OH-9 | (i) | (t) | (t) | (i) |

| Substance No. Proton | 14[c,n] | 15[c] | 16[c] | 17[c] |
|---|---|---|---|---|
| H-1 | — | 7.91 dd | 7.89 d | 7.92 d |
| H-2 | 7.31 t | 7.72 t | 7.72 t | 7.72 t |
| H-3 | | 7.32 dd | 7.32 d | 7.31 t |
| H-7 | 5.24 bs | 5.51 m | 5.18 m | 5.09 m |
| H-8α | 2.1-2.4 m | 2.25 m | (i) | (i) |
| H-8β | | | (i) | (i) |
| H-10 | 4.30 s | 4.99 s | 4.98 s | 5.02 s |
| H-13α | 1.47 m | 1.63 m | (i) | (i) |
| H-13β | 1.84 m | 1.74 m | (i) | (i) |
| H$_3$-14 | 1.13 t | 1.12 t | | |
| H-1' | 5.55 bs | 5.44 d; 5.41 d | 5.41 | 5.43 |
| H-2' | | 1.85 m | (i) | (i) |
| H-3' | | 2.71 m; 2.68 m | (i) | (i) |
| H-4' | 3.81 bs | 3.60 bs; 3.57 bs | 3.76 bs | 3.71 bs |
| H-5' | 4.17 q | 4.07 q; 3.93 q | 3.93 q | 3.88 q |
| H-6' | 1.28 d | 1.39 d; 1.33 d | (i) | (i) |
| N—CH$_3$ | 2.99 s | 2.34 s; 2.33 s | 2.32 s | 2.31 s |
| OH-1 | 12.31[k]bs | — | — | — |
| OH-4 | 12.34[k]bs | (t)  (t) | (t) | (t) |
| OH-6 | 12.84 bs | (t)  (t) | (t) | (t) |
| OH-11 | 13.00 bs | (t)  (t) | (t) | (t) |
| OH-9 | | 3.65 bs | (t) | (t) |

TABLE 3

400 MHz $^1$H NMR data of various compounds of the formula I with tetramethylsilane as internal standard
The substance numbers in the first line correspond to the relevant example numbers; the indices (a) to (q) serve for more detailed characterization:

abbreviations  s: singlet
d: doublet
t: triplet
q: quartet
dd: doublet of doublets
bs: broad singlet (a) N-Pentyl CH$_3$: 0.84 t
(b) N-Hexyl CH$_3$: 0.83 t
(c) N-Heptyl CH$_3$: 0.84 t
(d) N-Octyl CH$_3$: 0.84 t
(e) NCH$_2$PhCl: β: 3.58 d; α: 3.38 d; Ph: 7.24 d (2H); 7.14 d (2H)
(f) NCH$_2$PhBr: β: 3.56 d; α: 3.36 d; Ph: 7.39 d (2H); 7.08 d (2H)
(g) NCH$_2$PhNO$_2$: β: 3.70 d; α: 3.56 d; Ph: 8.14 d (2H);

TABLE 3-continued 7.40 d (2H)
(h) NCH₂PhCN: β: 3.66 d; α: 3.49 d;
(i) Shaken with sodium bicarbonate/dichloromethane
(k) Pentyl CH₃: 0.84 t
(l) Ph-CH₂β: 3.65 d, 3.64 d; Ph-CH₂α: 3.45 d, 3.42 d
(m) Pentyl CH₃: 0.84 t; 0.80 t
(n) NCH₂CN: 3.51
(o) OCH₃: 4.07 s (3H)
(p) Mixture of 13-epimers; the stated data relate to the epimer which is predominantly formed
(q) 14-H₃ of the inor 13-epimer: 1.28 d

| Substance No. Proton | 18[a] | 19[b] | 20[c] | 21[d] |
|---|---|---|---|---|
| H-1 | 7.87 dd | 7.86 dd | 7.88 dd | 7.87 dd |
| H-2 | 7.71 t | 7.70 t | 7.71 t | 7.71 t |
| H-3 | 7.32 dd | 7.31 dd | 7.32 dd | 7.32 dd |
| H-7 | 5.14 m | 5.13 m | 5.14 m | 5.14 m |
| H-8α | 2.11 dd | 2.11 dd | 2.13 dd | 2.11 dd |
| H-8β | 2.26 d | 2.26 d | 2.26 d | 2.26 d |
| H-10 | 4.90 s | 4.90 s | 4.91 s | 4.90 s |
| H-13α | 1.72–1.94 m | 1.72–1.94 m | 1.72–1.94 m | 1.72–1.94 m |
| H₃-14 | 1.12 t | 1.12 t | 1.12 t | 1.12 t |
| H-1' | 5.50 d | 5.49 bs | 5.50 bs | 5.50 bs |
| H-2' | 1.72–1.94 m | 1.72–1.94 m | 1.72–1.94 m | 1.72–1.94 m |
| H-3' | | | | |
| H-4' | 3.71 bs | 3.67 bs | 3.67 bs | 3.67 bs |
| H-5' | 4.08 q | 4.07 q | 4.07 q | 4.07 q |
| H₃-6' | 1.40 d | 1.41 d | 1.41 d | 1.41 d |
| N—CH₃ | 2.23 s | 2.18 s | 2.18 s | 2.18 s |
| OH-4 | 12.18 bs | | 12.13 bs | 12.1 bs |
| OH-6 | 12.81 bs | | 12.8 bs | 12.8 bs |
| OH-11 | | | 13.6 bs | 13.5 bs |
| OH-9 | 4.01 bs | 4.05 s | 4.05 s | 4.05 s |

| Substance No. Proton | 22[e] | 23[f] | 24[g] | 25[h] |
|---|---|---|---|---|
| H-1 | 7.87 dd | 7.87 dd | 7.88 dd | 7.89 dd |
| H-2 | 7.71 t | 7.71 t | 7.72 dd | 7.72 t |
| H-3 | 7.32 dd | 7.32 dd | 7.32 dd | 7.33 d |
| H-7 | 5.16 m | 5.16 m | 5.17 m | 5.17 m |
| H-8α | 2.13 dd | 2.13 dd | 2.13 dd | 2.14 dd |
| H-8β | 2.27 d | 2.27 d | 2.27 d | 2.26 d |
| H-10 | 4.92 s | 4.92 s | 4.92 s | 4.92 s |
| H-13α | 1.81 m | 1.79 m | 1.79 m | 1.79 m |
| H-13β | 1.84–1.98 m | 1.85–1.95 m | 1.84–1.98 m | 1.84–1.98 m |
| H₃-14 | 1.13 t | 1.13 t | 1.13 t | 1.13 t |
| H-1' | 5.53 m | 5.53 m | 5.55 bs | 5.54 bs |
| H-2' | 1.84–1.98 m | 1.85–1.95 m | 1.84–1.98 m | 1.84–1.98 m |
| H-3' | 2.60 dt | 2.59 dt | 2.65 dt | 2.63 dt |
| H-4' | 3.80 bs | 3.80 bs | 3.82 bs | 3.80 bs |
| H-5' | 4.12 q | 4.12 q | 4.14 q | 4.13 q |
| H₃-6' | 1.42 d | 1.42 d | 1.42 d | 1.42 d |
| N—CH₃ | 2.08 s | 2.07 s | 2.12 s | 2.10 s |
| OH-4 | 12.10 bs | 12.10 bs | 12.10 b | 12.12 bs |
| OH-6 | 12.82 bs | 12.82 bs | 12.82 bs | 12.85 bs |
| OH-11 | 13.60 bs | 13.60 bs | 13.60 bs | 13.61 bs |
| OH-9 | 4.01 bs | 4.01 s | 3.98 s | 3.98 s |

| Substance No. Proton | 26[i] | 27[i,k] | 28[l] | 29[m] |
|---|---|---|---|---|
| H-1 | 7.87 d | | 7.91 dd | 7.91 dd |
| H-2 | 7.71 t | 7.32 s | 7.71 t | 7.72 t |
| H-3 | 7.32 d | | 7.31 dd | 7.32 dd |
| H-7 | 5.14 m | 5.16 m | 5.19 m | 5.15 m |
| H-8α | | | | |
| H-8β | | | | |
| H-10 | 4.90 s | 4.91 s | 5.03 s | 5.00 s |
| H-13α | | | 1.74 m | |
| H-13β | | | 1.80–1.94 m | |
| H₃-14 | 1.12 t | 1.12 t | 1.13 t | 1.12 t |
| H-1' | 5.50 bs | 5.52 d | 5.54 bs; 5.50 d | 5.48 bs; 5.44 d |
| H-2' | | | 1.80–1.94 m | |
| H-3' | | | 2.58–2.70 m | |
| H-4' | 3.66 bs | 3.73 bs | 3.81 bs; 3.76 bs | 3.66 bs; 3.60 bs |
| H-5' | 4.07 q | 4.07 q | 4.10 q; 3.94 q | 4.04 q; 3.90 q |
| H₃-6' | 1.41 d | 1.40 q | 1.43 d; 1.36 d | 1.39 d; 1.35 d |

| | | | | | |
|---|---|---|---|---|---|
| N—CH₃ | 2.13 bs | 2.25 bs | 2.13 s; 2.10 s | 2.17 s; 2.16 s |
| OH-1 | | 12.32 bs | | |
| OH-4 | 12.13 bs | | 12.12 bs | 12.14 bs |
| OH-6 | 12.81 bs | 12.92 bs | 12.90 bs | 12.89 bs |
| OH-11 | 13.59 bs | | 13.74 bs | 13.71 bs |
| OH-9 | 4.06 | | | 3.66 bs |

| Substance No. Proton | 30[n] | 31[o] | 32[o,p] |
|---|---|---|---|
| H-1 | 7.90 dd | 8.02 d | 8.02 d |
| H-2 | 7.71 t | 7.77 t | 7.76 t |
| H-3 | 7.32 dd | 7.38 d | 7.37 t |
| H-7 | 5.16 m | 5.29 m | 5.28 s |
| H-8α | | | |
| H-8β | | | |
| H-10 | 5.01 s | 3.22 d (10β) 2.97 d (10α) | 3.19 d (10β) |
| H-13α | | | |
| H-13β | | | |
| H₃-14 | 1.12 t | 2.41 s | 1.32 d[q] |
| H-1' | 5.49 bd; 5.46 bd | 5.50 bs | 5.51 bd |
| H-2' | | 2.73 m | |
| H-3' | | | |
| H-4' | | 3.62 bs | 3.61 bs |
| H-5' | 4.10 q; 3.96 q | | 3.69 q |
| H-6' | 1.37 d; 1.34 d | 1.37 d | 1.37 d |
| N—CH₃ | 2.40 s; 2.36 s | 2.36 s | 2.34 s |
| OH-4 | 12.14 bs | | |
| OH-6 | 12.89 bs | | |
| OH-11 | 13.75 bs | | |

We claim:
1. An anthracycline derivative having the formula I or a a physiologically acceptable inorganic or organic acid salt thereof

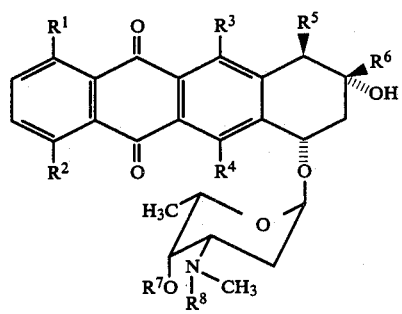

wherein
R¹ is hydrogen or a hydroxyl group,
R² is hydrogen or a hydroxyl or a methoxy group,
R³ is hydrogen or a hydroxyl group,
R⁴ is hydrogen or a hydroxyl group,
R⁵ is hydrogen, a hydroxyl or a methoxycarbonyl group, or a substituent of the formula II,

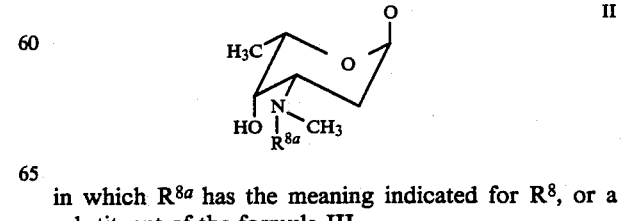

in which R⁸ᵃ has the meaning indicated for R⁸, or a substituent of the formula III,

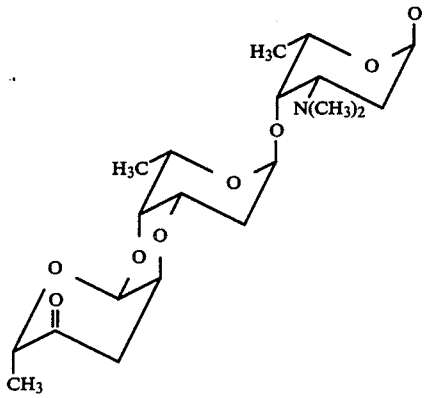

III $R^6$ is ethyl, hydroxymethylcarbonyl, hydroxymethylcarbonyl, $R^7$ is hydrogen or a substituent of the formula IV,

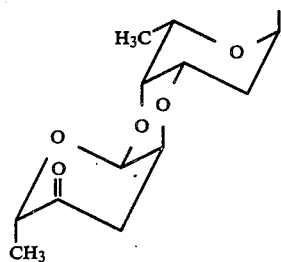

IV $R^8$ is hydrogen or a cyanomethyl group or a substituent of the formula $COR^9$ or $CH_2R^{10}$, $R^9$ being hydrogen, $CH_3$, $CF_3$ or $CCl_3$, and $R^{10}$ being $C_1$- to $C_8$-alkyl, substituted alkyl, phenyl or substituted phenyl, excepting the compound of the formula I in which $R^1=H$, $R^2=OH$, $R^3=H$, $R^4=OH$, $R^5=COOCH_3$, $R^6=CH_2CH_3$ and $R^7=R^8=H$, excepting the compound of the formula I in which $R^1=H$, $R^2=OCH_3$, $R^3=R^4=OH$, $R^5=H$, $R^6=COCH_3$ and $R^7=R^8=H$, excepting and, for the additional case where $R^8$ is a cyanomethyl group, those compounds in which $R^1$ is H, $R^2$ has the said meaning, $R^3$ is OH, $R^4$ is OH, $R^5$ is H, $R^6$ has the said meaning, and $R^7$ is H.

2. Anthracycline derivatives as claimed in claim 1, wherein $R^5$ is hydrogen or a hydroxyl or a methoxycarbonyl group, $R^7$ is hydrogen, and $R^8$ is hydrogen, cyanomethyl or a substituent of the general formula $COR^9$ with $R^9=H$, $CH_3$, $CF_3$ or $CCl_3$, or a substituent of the formula $CH_2R^{10}$, $R^{10}$ being $C_1$- to $C_8$-alkyl, substituted alkyl, phenyl or phenyl which is substituted in the ortho, meta or para position by methyl, ethyl, hydroxyl, methoxy, ethoxy, nitro, cyano, fluorine, chlorine or bromine.

3. Anthracycline derivatives as claimed in claim 1, in which $R^1=H$, $R^2=R^3=R^4=R^5=OH$, $R^6=CH_2CH_3$ and $R^7=H$.

4. Anthracycline derivatives as claimed in claim 1, in which $R^1=R^2=R^3=R^4=R^5=OH$, $R^6=CH_2CH_3$ and $R^7=H$.

5. Anthracycline derivatives as claimed in claim 1, in which $R^1=R^2=R^3=R^4=OH$, $R^5=COOCH_3$, $R^6=CH_2CH_3$ and $R^7=H$.

6. Anthracycline derivatives as claimed in claim 1, in which $R^1=H$, $R^2=R^3=R^4=OH$, $R^5=COOCH_3$, $R^6=CH_2CH_3$ and $R^7=H$.

7. Anthracycline derivatives as claimed in claim 1, in which $R^1$ is H, $R^2$ is OH, $R^3$ is H, $R^4$ is OH, $R^5$ is $COOCH_3$, $R^6$ is $CH_2CH_3$, $R^7$ is H, and $R^8$ is not identical to $R^7$.

8. Anthracycline derivatives as claimed in claim 1, in which $R^5$ is a substituent of the formula II, and $R^7$ is hydrogen, and $R^8$ and $R^{8a}$ are identical.

9. Anthracycline derivatives as claimed in claim 8, in which $R^1=H$, $R^2=R^3=R^4=OH$, $R^6=CH_2CH_3$ and $R^7=H$.

10. Anthracycline derivatives as claimed in claim 9, in which $R^1=OH$, $R^2=R^3=R^4=OH$, $R^6=CH_2CH_3$ and $R^7=H$.

11. Anthracycline derivatives as claimed in claim 1, in which $R^5$ is a substituent of the formula III, and $R^7$ is hydrogen.

12. Anthracycline derivatives as claimed in claim 11, in which $R^1=H$, $R^2=R^3=R^4=OH$ and $R^6=CH_2CH_3$.

13. Anthracycline derivatives as claimed in claim 11, in which $R^1=OH$, $R^2=R^3=R^4=OH$ and $R^6=CH_2CH_3$.

14. Anthracycline derivatives as claimed in claim 1, in which $R^7$ is a substituent of the formula IV, $R^8$ is $CH_3$, $R^5$ is a substituent of the formula II, and in which $R^{8a}$ is not identical to $R^8$.

15. Anthracycline derivatives as claimed in claim 14, in which $R^1=H$, $R^2=R^3=R^4=OH$ and $R^6=CH_2CH_3$.

16. Anthracycline derivatives as claimed in claim 14, in which $R^1=OH$, $R^2=R^3=R^4=OH$ and $R^6=CH_2CH_3$.

* * * * *

UNITED STATES PATENT AND TRADEMARK OFFICE
CERTIFICATE OF CORRECTION

PATENT NO. : 4,948,880

DATED : August 14, 1990

INVENTOR(S) : Peter Hermentin, et al.

It is certified that error appears in the above-identified patent and that said Letters Patent is hereby corrected as shown below:

Claim 1, column 23, lines 18 and 19, "hydroxymethylcarbonyl, hydroxymethylcarbonyl" should be deleted.

Signed and Sealed this

Twenty-first Day of July, 1992

Attest:

DOUGLAS B. COMER

*Attesting Officer*   *Acting Commissioner of Patents and Trademarks*